United States Patent [19]

Hirschfeld

[11] Patent Number: 5,913,679
[45] Date of Patent: Jun. 22, 1999

[54] LIGATURE TOOL

[76] Inventor: John W. Hirschfeld, 1404 NE. 16th Pl., Gainesville, Fla. 32609

[21] Appl. No.: 08/798,731

[22] Filed: Jan. 13, 1997

[51] Int. Cl.[6] .................................................... A61C 3/00
[52] U.S. Cl. ...................................................... 433/3
[58] Field of Search ................................................ 433/3, 4

[56] References Cited

U.S. PATENT DOCUMENTS

| | | | |
|---|---|---|---|
| 4,040,187 | 8/1977 | Cardena | 433/3 |
| 4,277,236 | 7/1981 | Kurz | 433/3 |
| 4,472,137 | 9/1984 | Barone | 433/3 |
| 4,668,186 | 5/1987 | Bally et al. | 433/3 |

*Primary Examiner*—John J. Wilson
*Attorney, Agent, or Firm*—John B. Dickman, III

[57] ABSTRACT

A ligature tool for applying elastic ligatures onto an orthodontic bracket without patient discomfort by automatically picking up one ligature at a time, expanding it over a tip and snapping it onto a bracket, without pressing against the bracket. The ligature tool has a ligature tip that is pre-loaded with a stack of ligatures where the ligature tip is replaceable with tips having larger or smaller ligatures.

10 Claims, 3 Drawing Sheets

LIGATURE TOOL

BACKGROUND OF THE INVENTION

This invention relates to a ligature tool for applying small elastic ligatures onto orthodontic brackets without patient discomfort, and in particular, to a ligature tool to automatically pick up one ligature at a time, expand it over a tip and snap it onto the bracket.

Orthodontists move teeth by applying low level forces over long periods of time. Brackets are directly bonded to the teeth and a force is applied to the tooth by an arch wire which passes through a slot in each bracket. The arch wire is held in the slot of the bracket with an elastic ligature (O-ring) and extends from bracket to bracket. The brackets are often of different sizes and shapes, depending on the size and position of the individual teeth. The ligatures are generally replaced once or twice a month when the arch wires are adjusted or changed as the teeth move.

Presently, the elastic ligatures are usually applied by a hemostat. Orthodontists and their assistants have become very skilled in using the hemostat and are surprisingly fast in picking up a ligature and stretching it around the bracket. However, this requires concentration and eye movement from the pick-up point to the mouth. Patients with sensitive teeth experience discomfort as the ligature is stretched around the bracket. In addition, to add to the discomfort, teeth undergoing orthodontic treatment are often sore and sensitive to pressure.

The American Orthodontic company has sold a simple "U" shaped tool called a "Speedo Plastic Ligature Director" for applying the ligatures. The ligature is pre-loaded onto the "Speedo" with a hemostat and then rolled off the "Speedo" onto the bracket. Using the "Speedo" reduces the discomfort to the patient but does not save time overall. Both the hemostat and the "Speedo" are simple, inexpensive and easily sterilized.

U.S. Pat. No. 4,277,236 is directed to a ligature tool which automatically picks up the first ligature and applies the ligature without applying pressure to a patient's bracket. While this patent may have the advantages of the present ligature tool, the patented tool is far more mechanically difficult to operate.

U.S. Pat. Nos. 4,040,187 and 4,472,137 disclose ligature tools of general interest, however they do not pick up the first ligature and they do apply pressure against the bracket.

It is the principle object of this invention to provide a ligature tool which picks up the first ligature and transfers it to a bracket without applying pressure to the tooth.

Another object is to provide a ligature tool that is mechanically simple to operate.

Another object is to provide a ligature tool that has a tip (pre-loaded with a plurality of ligatures) that is easily replaced.

SUMMARY OF THE INVENTION

The present invention provides a ligature tool which consists of is simple to operate which picking up the first ligature from a line of ligatures and applying it to an orthodontic bracket without any pressure to a patient's bracket.

The ligature tool has a stationary barrel connected to a stationary shaft, which carries a replaceable tip and a pair of finger rings. A slidable barrel with a thumb ring reciprocates through the stationary barrel. A pair of pivotal arms are mounted on the slidable barrel to move the forward most ligature along the removable tip.

The removable tip consists of a shaft for storing a plurality of ligatures, an inclined ramp for expanding a ligature and a tip end which fits over a bracket and allows the expanded ligature to snap off of the tip end and onto the bracket. The pair of pivotal arms are held against the top shaft with springs, the pivotal arms can be moved along the shaft expanding the ligature on the inclined ramp and push it off the tip end onto the bracket. The tip end includes guiding ridges and the pivotal arms include grooves which fit over the ridges to keep the pivotal arms in contact with the tip end. The tip end has two slots which are positioned over an orthodontic arch wire allowing the tip end to fit over the bracket.

A yoke pivotally mounted on the slidable barrel has a slotted end which pulls the stack of ligatures rearward against a stop with the pivotal arm tips spaced one ligature behind the yoke. Each pivotal arm tip includes grooves which permit the tips to surround the first ligature while it is being advanced along the tip shaft toward the tip end. Also, these grooves fit over ridges in the tip end and keep the pivotal arms in close contact with the tip end while the ligature is expanded over the tip end. The arms are held against the shaft by springs.

The stationary shaft has a cam surface to allow the yoke spring to retract the yoke away from the shaft when the arms are advanced to the inclined ramp of the tip. The yoke is mounted on the sliding barrel in slots and held with pivot pins which allow the yoke to pivot away from and avoid contact with the bracket while the ligature is being pushed off the tip end.

DESCRIPTION OF THE INVENTION

Figure 1:
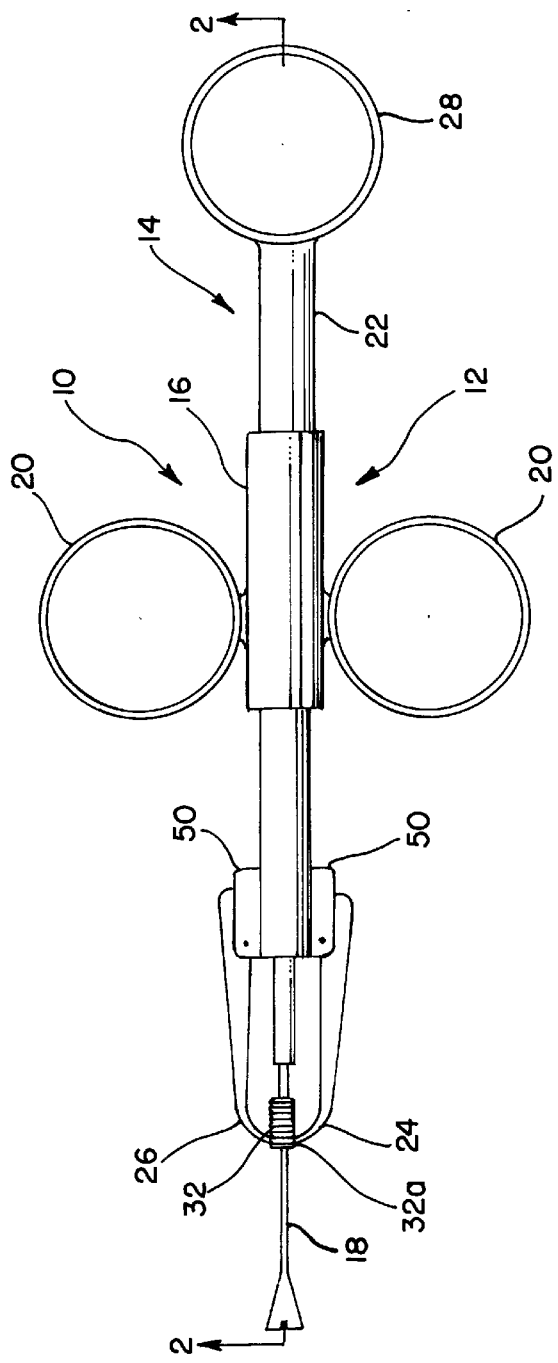
FIG. 1 is a top plan view of a ligature tool of the invention.
Figure 2:
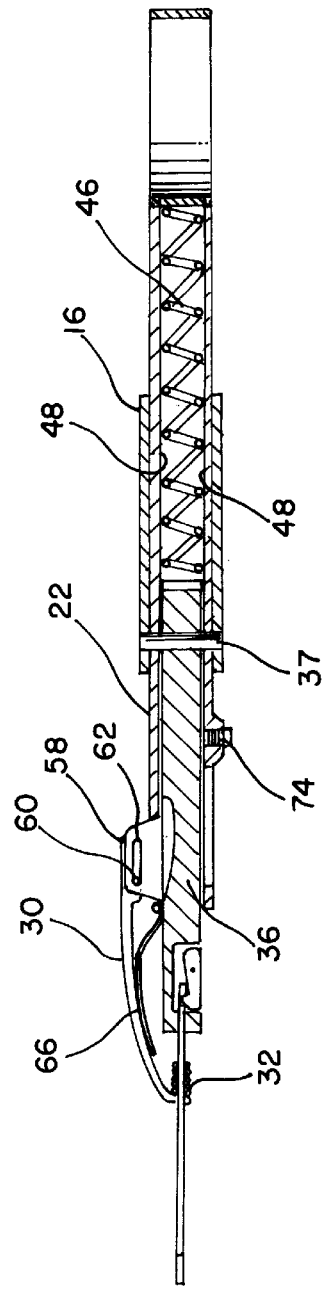
FIG. 2 is a cross-section side view taken along the line 2—2 of FIG. 1.
Figure 3:
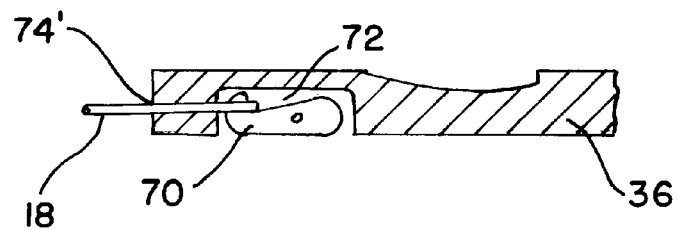
FIG. 3 is a partial cross-section side view of a ligature tip locking trip.
Figure 4:
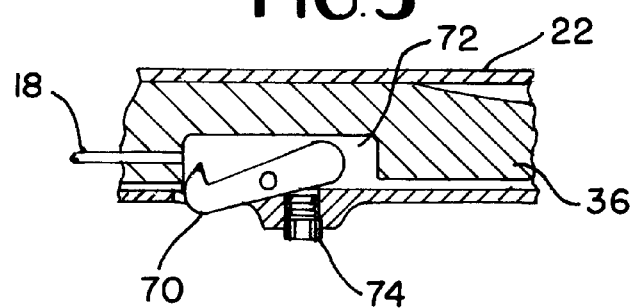
FIG. 4 is a partial cross-section side view of a ligature tip locking trip in the release position.

Referring to the drawings, FIGS. 1 to 10, there is shown in FIG. 1 a ligature tool 10 for applying ligatures which are small elastic O-rings used by orthodontists to hold the arch wire in a slot in to the dental bracket to straighten teeth, by automatically picking up one ligature at a time and expanding it onto a bracket without causing patient discomfort. In general, ligature tool 10 has two main assemblies, stationary 12 and sliding 14. The stationary assembly 12, includes a barrel 16, a ligature tip 18 and two finger rings 20. The sliding assembly 14 includes a slidable barrel 22 with pivotal arms 24 and 26, and thumb ring 28. A yoke 30 pivotally mounted on top of slidable barrel 22 pulls a stack of ligatures 32, FIGS. 5 and 6, rearward against a stop 34 of a stationary shaft 36 affixed to stationary barrel 16 by a pair of machine screws, or a pin 38a.

The ligature tip 18 has a triangular tip end 38 with two slots 40 to fit over the orthodontic arch wire (not shown) thereby allowing the tip end 38 to fit over a bracket. Tip end 38 is integrally formed with a shaft 42, which has a pair of opposed grooves 44, FIG. 9, to prevent the ligature tip 18 from rotating or separating from stationary shaft 36, to be described in more detail later.

Stationary assembly 12 is held stationary by the finger rings 20 such that the stationary shaft and ligature tip 18 do not move. The slidable assembly 14 moves against the pressure of a spring 46 inside the slidable barrel 22 to bear against thumb ring 28 and the rear of stationary shaft 36. Pin 38a which secures the stationary shaft 36 to stationary barrel 16, reciprocates in slots 48 of slidable barrel 22 to guide the slidable assembly 14.

Pivotal arms 24 and 26 are attached to the slidable barrel 22 by a pair of identical supports 50 and pins 52. Hidden springs force tips 54 and 56 against ligature tip shaft 42 to engage the further most ligature 32a and move it along the ligature tip shaft 42 to tip end 38 and over the tip end and on to the orthodontic bracket when the slidable assembly 14 is moved toward ligature tip end 38.

Figure 5:
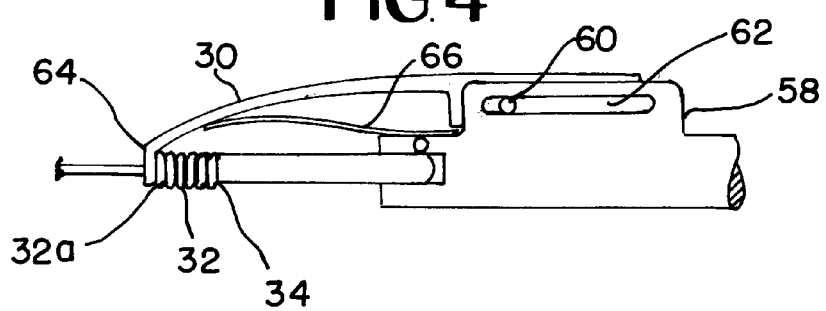
FIG. 5 is a partial side view of a ligature guiding and dispensing mechanism.
Figure 6:
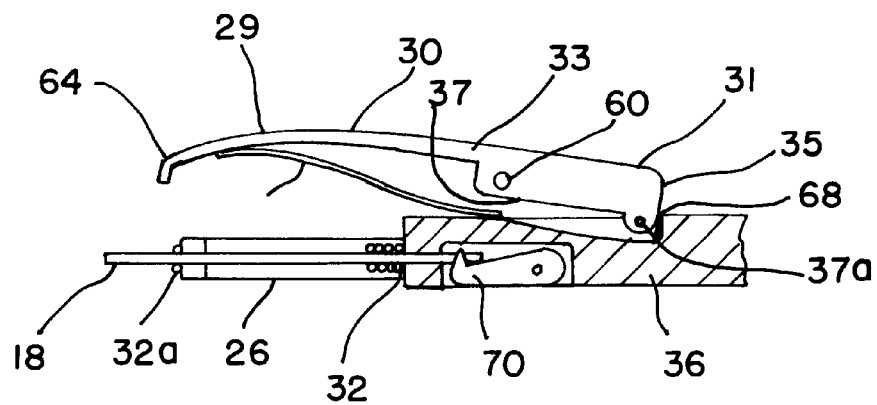
FIG. 6 is a partial cross-section side view of a ligature guiding mechanism pivoted out of the way to allow dispensing of a ligature.
Figure 7:
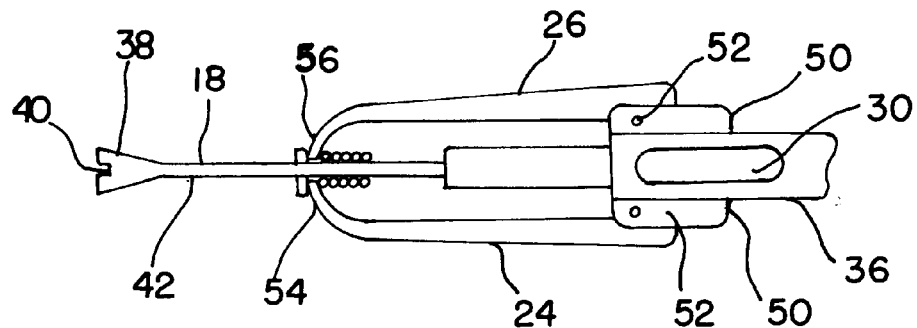
FIG. 7 is a partial top plan view showing a dispensing mechanism of the invention.
Figure 8:
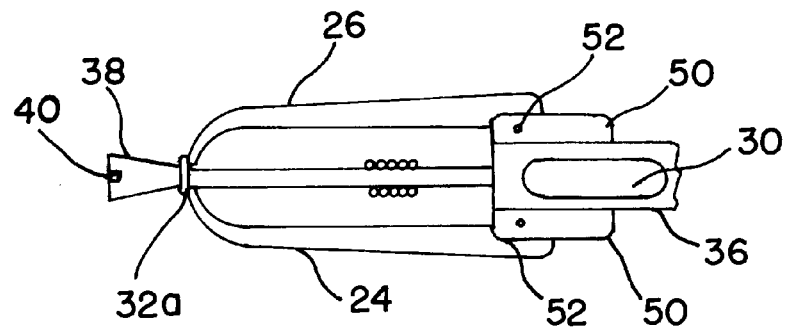
FIG. 8 is a partial top plan view showing the dispensing mechanism of FIG. 7 dispensing a ligature.
Figure 9:
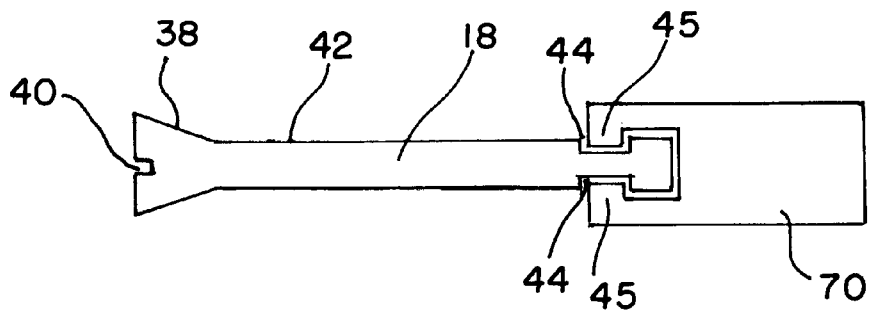
FIG. 9 shows a top plan view of a ligature tip and locking trip of the invention.
Figure 10:
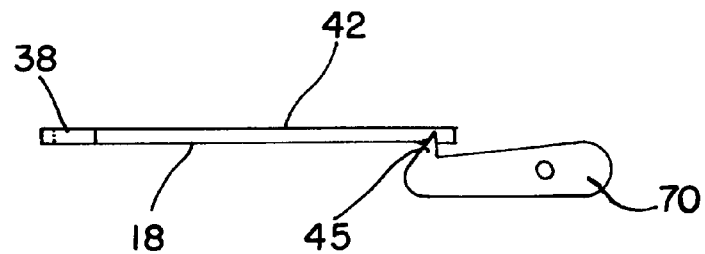
FIG. 10 is a side plan view of FIG. 9 showing a ligature tip with the locking trip engaging the ligature tip.

Yoke 30 is also pivotally mounted on slidable barrel 22 by a pair of supports 58 and a pin 60. Supports 58 have slots 62 in which the yoke reciprocates to move the yoke 30 out of the way of the bracket when the ligature is expanded over the tip end and when removing the ligature tip 18. Yoke 30 has a right angle end 64 with a forked end, not shown, to fit over tip shaft 42 to move the ligature stack 32 rearward. A spring 66 pressing against the yoke 30 moves the yoke out of the way when a single ligature 32a reaches the tip end 38 to permit the arms 24 and 26 to push the ligature off the end, as shown in FIGS. 7 and 8. To move yoke 30 out of the way, the stationary shaft 36 has an indented area 68, FIG. 6, to allow the yoke 30 to pivot under the pressure of spring 66. When the yoke is to be moved out of the way, it's pins 60 move rearwardly in slots 62, as shown in FIG. 5. Yoke 30 has a neck 29 with a right angle slotted end 64 on one end and a rectangular enlarged area 31 on the other end. The rectangular enlarged area 31 has a forward end 33 connected to the neck 29, a rear end 35 with a lower flat edge 37 and a pivot point 37a at the lower rear of 31. Pin 60 is located in the rectangular enlarged area 31 close to the forward end 33. When yoke 30 is moved forward by shaft 22, the pivot point 37a slides into indented area 68 of shaft 36 allowing spring 66 to pivot the right angled slotted end 64 around pin 60, away from the tip shaft 18. As shaft 22 continues to move forward and arms 24 and 26 advance the ligature 32a over the tip end 38, the slotted end 64 of yoke 30 will press against the tooth mounted bracet or it's arch wire, causing pin 60 to move rearward in slots 62 and allowing the slotted end 64 of yoke 30 to move away from the tooth mounted bracket and arch wire. The rearward movement of yoke 30 provided by slots 62 is necessary to get yoke 30 out of the way so that slots 40 in arms 24 and 26 can fit over the arch wire while ligature 32a is pushed onto the bracket.

After ligature 32a has been placed on the bracket, thumb pressure is released on ring 28 and spring 46 moves the shaft 22 and yoke 30 rearward. As yoke 30 moves rearward along shaft 36, pivot point 37a slides out of indented area 68 of shaft 36, which causes pin 60 to slide forward in slots 62 and causes yoke 30 to pivot inward against spring 66, until slotted end 64 of yoke 30 is over tip shaft 18.

Ligature tip 18 is held in stationary shaft 36 by a pivotal catch 70 with fingers 44 with fingers 45 as shown in FIGS. 3 and 4 and 9 and 10. Pivotal catch 70 is housed in a cut-out 72 in line with a hole 74 to allow the catch to engage the grooves 45. Catch 70 is spring biased such that when pivoted, the ligature tip 18 is released. A push button 74, operated by a spring which is not shown or forms part of the invention, aligns with the cut-out 72 to pivot the catch 70 when the slidable assembly 14 is moved forward to align the two. With the push button 74 engaging the catch 70, the push button 74 also engages the rear of the cut-out 72 to lock the slidable assembly 14 in the forward position. In this position, the rear of arms 24 and 26 are squeezed by the operator to pivot them out of the way to remove ligature tip 18.

In operation, yoke 30 is positioned in front of the first ligature 32a of stack 32 and the tips 54 and 56 of arms 24 and 26, respectively, engage the rear of the first ligature where the yoke 30 presses the ligature stack 32 rearward and further presses a single ligature against arms 24 and 26 as the ligature is moved along the shaft 42 of ligature tip 18. To move the ligature 32a along shaft 42, the stationary barrel is held still by finger rings 20 while thumb ring 28 is pressed against spring 46 to move slidable barrel 22 over shaft 36. This moves arms 24 and 26 and yoke 30 toward tip end 38. When the ligature 32a reaches tip end 38, yoke 30 is pivoted out of the way by 37a sliding in groove 68 to release ligature 32a.

When it is necessary to add additional stacks of ligatures to the ligature tip, the slidable assembly is moved forward and push button 74 engages cut-out 72 to lock the assembly 14 in the forward position. At the same time, push button 74 pivots catch 70 to release it from grooves 44 of the tip shaft 42. Arms 24 and 26 are squeezed to spread them apart, thereby allowing the tip 18 to be removed.

While only one embodiment has been disclosed, for a full understanding of the invention, the drawings, description and claims should be considered.

I claim:

1. An orthodontic ligature tool for applying elastic ligatures to brackets on the teeth of a patient for retaining an arch wire in the brackets, sid ligature tool comprising:

a first assembly having a stationary barrel with a holding means, and a ligature tip means;

a second assembly slidable within said stationary barrel having a sliding barrel with pivotal arms and a pivotal yoke to separate and move a single ligature along said ligature tip means;

a shaft means connected to said stationary barrel to support said ligature tip means;

said ligature tip means having a shaft with a triangular shaped end and means to engage a stationary shaft and lock against removal and means to release said ligature tip from said first assembly;

said pivotal arms on said slidable barrel have tip ends to separate and move a single ligature tip means, said pivotal arms moving along said ligature tip shaft and said triangular shaped end to dispense onto an orthodontic bracket;

said yoke on said slidable barrel engages the first ligature of a stack of ligatures and presses it rearward; as said arms move said first ligature along said ligature tip means, said yoke being pivotal to move away from said ligature tip shaft when said arms move said first ligature to said triangular shaped end in order to release said ligature.

2. An orthodontic ligature tool as in claim 1, wherein said yoke having pivot pins slidably mounted in slots to allow said yoke to slide rearward away from the tip end in order to avoid contact between the yoke and the tooth mounted brackets.

3. An orthodontic ligature tool as in claim 2 wherein said shaft means connected to said stationary barrel has a means to engage and lock including a cut-out with a catch means to engage said ligature tip shaft and lock said shaft to said shaft.

4. An orthodontic ligature tool as in claim 2 wherein said shaft means connected to said stationary barrel has a locking means to engage and lock said ligature tip shaft to said shaft means, said locking means including a cut-out in said shaft means and a catch housed in said cut-out which engages said ligature tip shaft.

5. An orthodontic ligature tool as in claim 4 wherein said slidable barrel has a catch operating means to pivot said catch when aligned with said cut-out in said stationary shaft, whereas said operating means locks in said cut-out to hold said second assembly in a forward position.

6. An orthodontic ligature tool as in claim 5 wherein said pivotal arms pivot to separate said tips to allow said ligature tip to be removed when said ligature shaft has been released from said stationary shaft.

7. An orthodontic ligature tool as in claim 6 wherein said stationary shaft has an indentation to allow said pivotal yoke to pivot away from said ligature tip shaft.

8. An orthodontic ligature tool as in claim 7 wherein said pivotal yoke is pivotally mounted on said stationary shaft, where said stationary shaft has mounts with slots for said pivotal yoke to pivot and reciprocate away from said ligature tip shaft.

9. An orthodontic ligature tool tip as in claim 1, wherein said triangular shaped end includes a ridge on each of the two edges which join the shaft, for the purpose of guiding the pivotal arms and keeping said arms from sliding sideways off the edges of the triangular shaped tip end while the ligature is being expanded and dispensed over the tip end.

10. An orthodontic ligature tool tip as in claim 1, wherein the tip shaft end has a pair of opposed grooves to prevent the ligature tip from rotating in or separating from the rest of the ligature tool.

\* \* \* \* \*